(12) United States Patent
Shelso

(10) Patent No.: US 7,470,282 B2
(45) Date of Patent: Dec. 30, 2008

(54) STENT GRIP AND SYSTEM FOR USE THEREWITH

(75) Inventor: Susan I. Shelso, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 506 days.

(21) Appl. No.: 10/611,551

(22) Filed: Jun. 30, 2003

(65) Prior Publication Data

US 2004/0267346 A1  Dec. 30, 2004

(51) Int. Cl.
*A61F 2/06* (2006.01)

(52) U.S. Cl. .................................................... 623/1.12

(58) Field of Classification Search ............. 623/1.11, 623/1.12, 1.3, 1.23; 606/108, 194; 600/585
See application file for complete search history.

(56) References Cited

U.S. PATENT DOCUMENTS

| | | | |
|---|---|---|---|
| 4,503,569 A | 3/1985 | Dotter | 3/1.4 |
| 4,733,665 A | 3/1988 | Palmaz | 128/343 |
| 4,950,227 A | 8/1990 | Savin et al. | 604/8 |
| 5,026,377 A | 6/1991 | Burton et al. | 606/108 |
| 5,290,295 A | 3/1994 | Querals et al. | 606/108 |
| 5,409,495 A | 4/1995 | Osborn | 606/108 |
| 5,484,444 A | 1/1996 | Braunschweiler et al. | |
| 5,534,007 A | 7/1996 | St. Germain et al. | |
| 5,693,066 A | 12/1997 | Rupp et al. | 606/198 |
| 5,702,418 A * | 12/1997 | Ravenscroft | 623/1.11 |
| 5,707,376 A | 1/1998 | Kavteladze et al. | |
| 5,709,703 A | 1/1998 | Lukic et al. | 606/198 |
| 5,725,549 A | 3/1998 | Lam | |
| 5,733,325 A | 3/1998 | Robinson et al. | |
| 5,746,745 A | 5/1998 | Abele et al. | 606/108 |
| 5,762,631 A | 6/1998 | Klein | |
| 5,772,669 A | 6/1998 | Vrba et al. | |
| 5,776,142 A | 7/1998 | Gunderson | 606/108 |
| 5,836,965 A | 11/1998 | Jendersee et al. | |

(Continued)

FOREIGN PATENT DOCUMENTS

EP   0819411   1/1998

(Continued)

OTHER PUBLICATIONS

Schetsky, L., "Shape Memory Alloys," Encyclopedia of Chemical Technology (3rd ed.), John Wiley & Sons, 1982, vol. 20, pp. 726-736.

(Continued)

*Primary Examiner*—(Jackie) Tan-Uyen T. Ho
*Assistant Examiner*—Melanie Tyson
(74) *Attorney, Agent, or Firm*—Crompton, Seager & Tufte, LLC

(57) ABSTRACT

A method and apparatus for reducing the longitudinal aspect of the catheter to stent force having at least one grip member for use with a stent delivery system. The grip engages a stent in the unexpanded state prior to delivery of the stent by retracting a stent retaining sheath. The grip has a body region having an outer diameter, a first end and a second end. The outer diameter of the first end is greater than the outer diameter of the second end. The grip is at least partially constructed from a polymeric material.

16 Claims, 3 Drawing Sheets

U.S. PATENT DOCUMENTS

| | | | |
|---|---|---|---|
| 5,913,871 A | 6/1999 | Werneth et al. | 606/194 |
| 5,935,135 A | 8/1999 | Bramfitt et al. | 606/108 |
| 5,941,908 A | 8/1999 | Goldsteen et al. | |
| 5,944,726 A | 8/1999 | Blaeser et al. | |
| 5,954,729 A | 9/1999 | Bachmann et al. | 606/108 |
| 5,968,069 A | 10/1999 | Dusbabek et al. | 606/194 |
| 5,976,155 A | 11/1999 | Foreman et al. | |
| 6,007,543 A | 12/1999 | Ellis et al. | |
| 6,007,545 A | 12/1999 | Venturelli | 606/108 |
| 6,027,510 A | 2/2000 | Alt | |
| 6,051,001 A | 4/2000 | Borghi | 606/108 |
| 6,053,943 A | 4/2000 | Edwin et al. | |
| 6,066,169 A | 5/2000 | McGuinness | |
| 6,077,273 A | 6/2000 | Euteneuer et al. | |
| 6,077,295 A | 6/2000 | Limon et al. | 623/1 |
| 6,077,297 A | 6/2000 | Robinson et al. | 623/1.11 |
| 6,106,530 A | 8/2000 | Harada | |
| 6,110,180 A | 8/2000 | Foreman et al. | |
| 6,120,522 A | 9/2000 | Vrba et al. | |
| 6,123,712 A | 9/2000 | Di Caprio et al. | 606/108 |
| 6,149,996 A * | 11/2000 | Helgerson et al. | 428/36.9 |
| 6,159,227 A | 12/2000 | De Caprio et al. | 606/192 |
| 6,168,617 B1 | 1/2001 | Blaeser et al. | |
| 6,203,558 B1 | 3/2001 | Dusbabek et al. | 606/198 |
| 6,214,036 B1 | 4/2001 | Letendre et al. | 623/1.11 |
| 6,228,110 B1 | 5/2001 | Munsinger | |
| 6,254,632 B1 | 7/2001 | Wu et al. | 623/1.15 |
| 6,258,099 B1 | 7/2001 | Mareiro et al. | 606/108 |
| 6,264,683 B1 | 7/2001 | Stack et al. | 623/1.11 |
| 6,280,412 B1 | 8/2001 | Pederson, Jr. et al. | 604/103.07 |
| 6,296,660 B1 | 10/2001 | Roberts et al. | |
| 6,302,906 B1 | 10/2001 | Goicoechea et al. | |
| 6,309,402 B1 | 10/2001 | Jendersee et al. | |
| 6,322,586 B1 | 11/2001 | Monroe et al. | 623/1.11 |
| 6,325,814 B1 | 12/2001 | Euteneuer et al. | |
| 6,331,188 B1 | 12/2001 | Lau et al. | |
| 6,350,277 B1 | 2/2002 | Kocur | |
| 6,371,962 B1 | 4/2002 | Ellis et al. | |
| 6,375,676 B1 | 4/2002 | Cox | |
| 6,380,457 B1 | 4/2002 | Yurek et al. | |
| 6,391,032 B2 | 5/2002 | Blaeser et al. | |
| 6,391,050 B1 | 5/2002 | Broome | |
| 6,391,051 B2 | 5/2002 | Sullivan, III et al. | 623/1.12 |
| 6,395,008 B1 | 5/2002 | Ellis et al. | |
| 6,395,017 B1 | 5/2002 | Dwyer et al. | |
| 6,419,685 B2 | 7/2002 | Di Caprio et al. | 606/192 |
| 6,428,566 B1 | 8/2002 | Holt | |
| 6,443,979 B1 | 9/2002 | Stalker et al. | |
| 6,468,298 B1 | 10/2002 | Pelton | 623/1.11 |
| 6,468,299 B2 | 10/2002 | Stack et al. | 623/1.11 |
| 6,494,906 B1 | 12/2002 | Owens | 623/1.11 |
| 6,506,201 B2 | 1/2003 | De Caprio et al. | 606/192 |
| 6,517,547 B1 | 2/2003 | Feeser et al. | 606/108 |
| 6,517,570 B1 | 2/2003 | Lau et al. | |
| 6,569,192 B1 | 5/2003 | Foreman et al. | 623/1.11 |
| 6,607,551 B1 | 8/2003 | Sullivan et al. | |
| 6,623,518 B2 | 9/2003 | Thompson et al. | |
| 6,660,031 B2 | 12/2003 | Tran et al. | |
| 6,682,553 B1 | 1/2004 | Webler | |
| 6,814,746 B2 | 11/2004 | Thompson et al. | |
| 6,816,997 B2 | 11/2004 | Teh et al. | |
| 6,896,180 B2 | 5/2005 | Miodunski et al. | |
| 6,960,227 B2 | 11/2005 | Jones et al. | |
| 7,001,422 B2 | 2/2006 | Escamilla et al. | |
| 7,152,605 B2 | 12/2006 | Khairkhahan et al. | |
| 2001/0007082 A1 | 7/2001 | Dusbabek et al. | |
| 2002/0049466 A1 | 4/2002 | Euteneuer et al. | |
| 2002/0055767 A1 | 5/2002 | Forde et al. | |
| 2002/0095204 A1 | 7/2002 | Thompson et al. | |
| 2002/0099435 A1 | 7/2002 | Stinson | 623/1.12 |
| 2002/0120321 A1 | 8/2002 | Gunderson et al. | 623/1.11 |
| 2002/0120322 A1 | 8/2002 | Thompson et al. | |
| 2002/0120323 A1 | 8/2002 | Thompson et al. | |
| 2002/0123794 A1 | 9/2002 | Ellis et al. | |
| 2002/0138081 A1 | 9/2002 | Blaeser et al. | |
| 2002/0151955 A1 | 10/2002 | Tran et al. | |
| 2002/0156519 A1 | 10/2002 | Di Caprio et al. | |
| 2003/0114912 A1 | 6/2003 | Sequin et al. | 623/1.11 |
| 2003/0212451 A1 * | 11/2003 | Cox et al. | 623/1.15 |
| 2004/0084523 A1 | 5/2004 | Miodunski et al. | |
| 2004/0204749 A1 * | 10/2004 | Gunderson | 623/1.12 |

FOREIGN PATENT DOCUMENTS

| | | |
|---|---|---|
| EP | 1157673 | 11/2001 |
| EP | 1369098 | 10/2003 |
| WO | 93/22986 | 11/1993 |
| WO | 94/15549 | 7/1994 |
| WO | 98/07390 | 2/1998 |
| WO | 00/71058 | 11/2000 |
| WO | 02/32496 | 4/2002 |
| WO | 02/41805 | 5/2002 |
| WO | 02/47582 | 6/2002 |

OTHER PUBLICATIONS

International Search Report, PCT/US2004/011023, Oct. 11, 2004.
Unpublished/Abandoned U.S. Appl. No. 08/697,453, filed Aug. 23, 1996 by Ellis et al.

* cited by examiner

STENT GRIP AND SYSTEM FOR USE THEREWITH

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates generally to a grip member for use with stent delivery systems and to systems employing one or more of such grips.

2. Description of Related Art

The use of stents, and other implantable medical devices such as grafts, stent-grafts, vena cava filters, etc, hereinafter referred to cumulatively as stents, to maintain the patency of bodily lumens is well known.

Stents are typically delivered via a catheter in an unexpanded configuration to a desired bodily location. Once at the desired bodily location, the stent is expanded and implanted in the bodily lumen.

Typically, a stent will have an unexpanded (closed) diameter for placement and an expanded (opened) diameter after placement in the vessel or the duct. Some stents are self-expanding; some stents are expanded mechanically with radial outward force from within the stent, as by inflation of a balloon; and some stents, known as hybrid stents, have one or more characteristics common to both self-expanding and mechanically expandable stents.

An example of a mechanically expandable stent and associated delivery system is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

A type of self-expanding stent is described in U.S. Pat. No. 4,503,569 to Dotter which issued Mar. 12, 1985, and discloses a shape memory stent which expands to an implanted configuration with a change in temperature. Self-expanding stents are constructed from a wide variety of materials including nitinol, spring steel, shape-memory polymers, etc.

In many stent delivery systems, particularly those used to deliver a self-expanding stent, the stent is typically retained on the catheter via a retention device such as a sheath. The stent may be deployed by retracting the sheath from over the stent. However it is known that in many cases when a sheath is withdrawn from a stent, particularly a self-expanding stent constructed of shape memory material, the individual struts or stent members of the stent will push outward as they expand back to their "remembered" shape. Often times, but undesirably, as the sheath is withdrawn from about the stent, the stent will tend to migrate longitudinally relative to the stent mounting region of the catheter. This migration is believed to be caused by a longitudinal component of the force that the stent delivery system exerts on the stent during withdrawal of the sheath. The tendency of the stent to migrate during sheath retraction may result in the imprecise delivery of the stent and/or distortion of the stent body.

It would thus be desirable to reduce the longitudinal component of the delivery system to stent force and/or provide a device for use in a stent delivery system that reduces or prevents stent migration during withdrawal of the stent retaining sheath.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

This invention may be embodied in a variety of forms. For example, in at least one embodiment, the invention is directed to a stent delivery system that reduces or eliminates the longitudinal component of the system to stent force, which may influence or cause migration of the stent or one or more components thereof relative to the catheter during withdrawal of the retaining sheath. In some embodiments the reduction in the longitudinal component of the system to stent force is accomplished by reducing or minimizing the potential space between the inner catheter shaft or member, upon which the stent is mounted prior to delivery, and the retractable outer sheath which overlays the stent prior to delivery.

In some embodiments the potential space between the sheath and inner member/stent is reduced by providing a stent delivery system with one or more stent grips or grip members which underlie at least a portion of a stent prior to delivery. A stent grip comprises an annular ring mounted to the catheter shaft. In some embodiments the stent grip has an end portion and a body portion, in the reduced or pre-delivery state the stent is disposed about the body portion and an end of the stent abuts the end portion of the stent grip.

In at least one embodiment the stent grip comprises a body portion having a tapered or varying diameter. In at least one embodiment the diameter of the body tapers from a first diameter at a first end of the body to a second smaller diameter at a second end of the body. In some embodiment a stent delivery system includes a single tapered grip or a pair of tapered grips wherein each grip is respectively positioned on the catheter shaft to underlie an end of the stent.

In at least one embodiment a stent delivery system comprises a single stent grip, wherein the single grip has a body which has a length substantially the same as that of the stent. In some embodiments, multiple grips have body portions that have a combined length that is substantially less than or equal to that of the stent. In some embodiments the invention is directed to a stent grip member for use in a stent delivery system wherein the stent grip is at least partially constructed of a polymer material. In some embodiments the material is preferably of a fairly soft durometer value to allow a stent to be effectively gripped or at least partially imbedded within the material of the grip.

In some embodiments a grip is insert molded, molded and then bonded to the catheter shaft, or otherwise formed separately or in conjunction with the catheter shaft or portion thereof.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
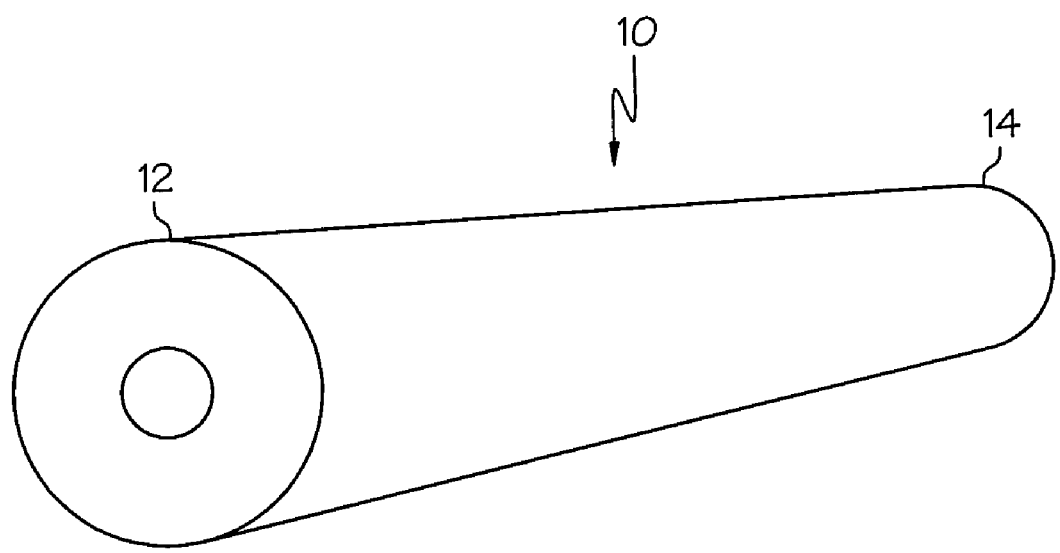
FIG. 1 is a perspective view of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As mentioned above the present invention is embodied in a variety of forms. For example, in the embodiment shown in FIG. 1 the invention is embodied in a stent retaining member or grip, indicated generally at 10, which has an outer diameter that tapers from a first, larger diameter at a first end 12 of the grip 10 to a second, smaller diameter at a second end 14 of the grip.

Figure 2:
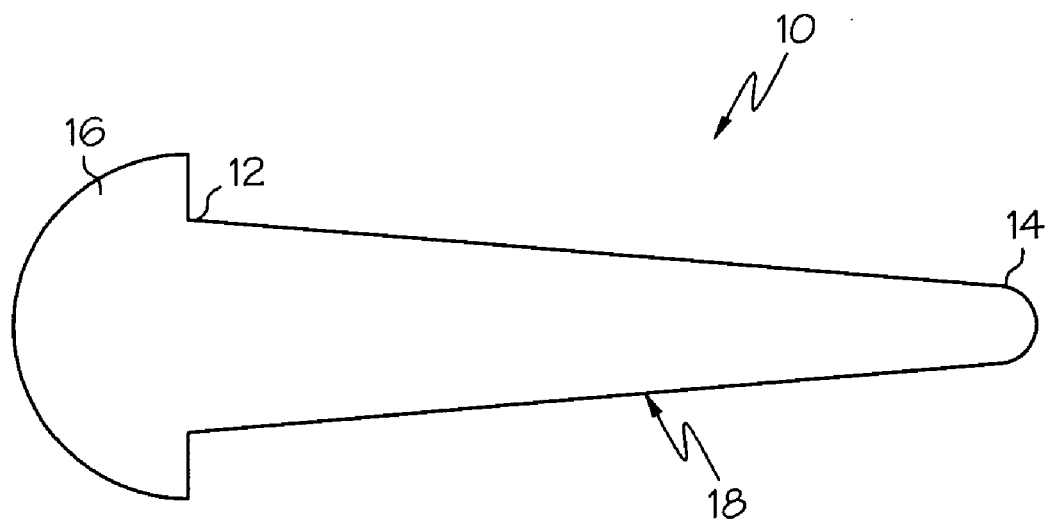
FIG. 2 is a cross-sectional side view of an embodiment of the invention.
Figure 3:
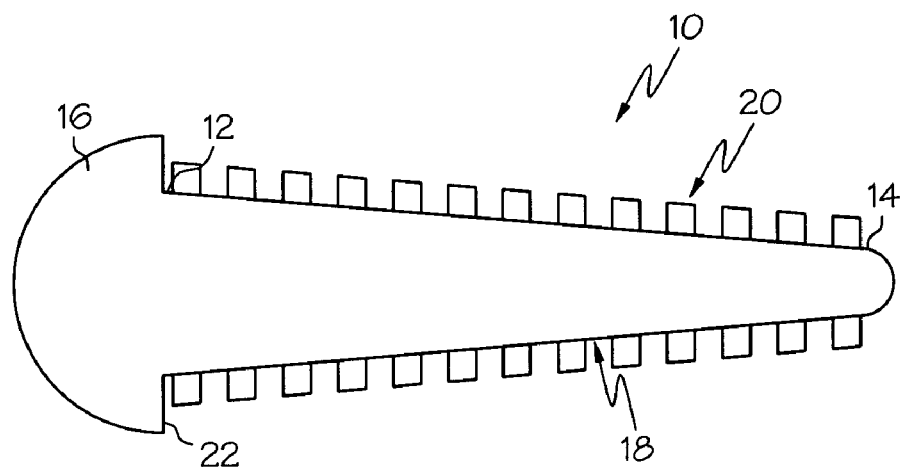
FIG. 3 is a cross-sectional side view of an embodiment of the invention.

In some embodiments, an example of which is shown in FIG. 2, the grip 10 includes a hub or dam 16 adjacent to the first end 12. At least a portion of the hub 16 has a diameter larger than the diameter of the grip body 18. In at least one embodiment such as is shown in FIG. 3 a stent 20 or other implantable medical device may be positioned adjacent to or butted up against an inner surface 22 of the hub 16 when the stent is disposed about the grip body 18 prior to expansion of the stent.

Figure 4:
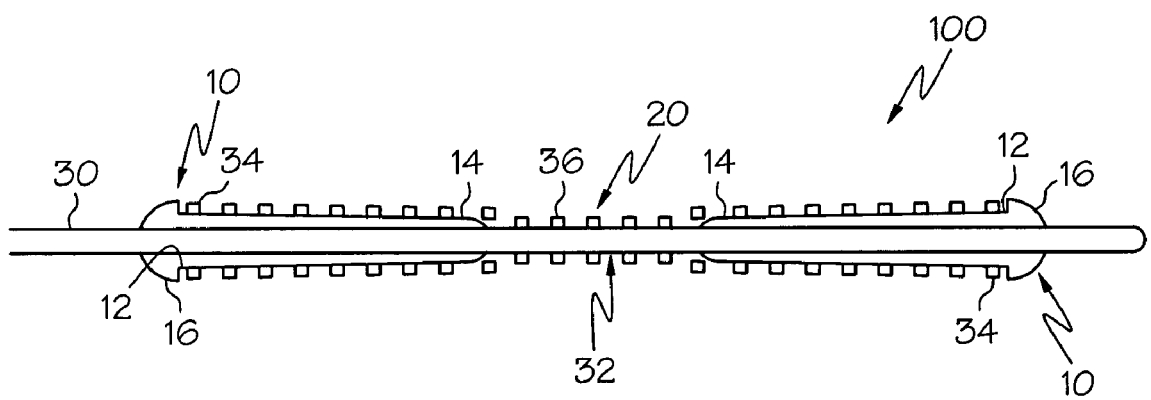
FIG. 4 is a cross-sectional side view of an embodiment of the invention.
Figure 5:
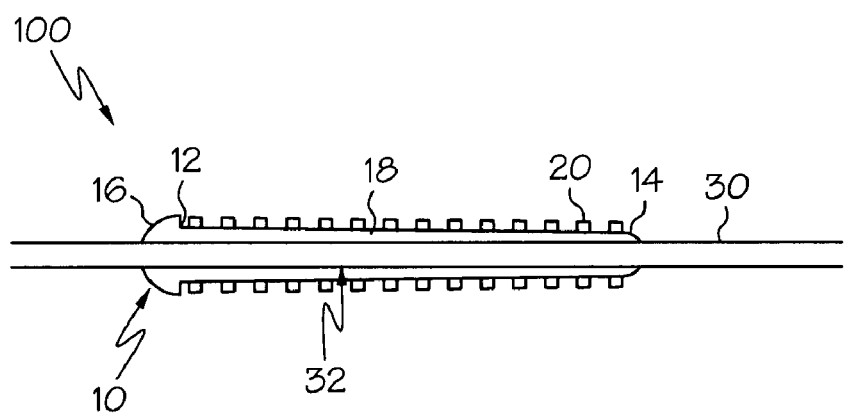
FIG. 5 is a cross-sectional side view of an embodiment of the invention.

As is illustrated in FIG. 4, in some embodiments, a stent delivery catheter, indicated generally at 100, comprises one or more grips 10. One or more grips 10 are engaged or incorporated onto the inner shaft or member 30 of the catheter 100. The position of the grips 10 on the inner member 30 substantially correspond to the area of the member which defines a stent mounting region 32. A stent 20 is disposed about the stent mounting region 32 and in the reduced or pre-delivery state is engaged to at least a portion of each grip 10.

Where a single grip 10 is utilized, such as is shown in FIG. 5 the body 18 of the grip underlies at least a portion of the stent. In at least one embodiment, the body 18 of the grip 10 has a length which is at least as long as that of the stent 20.

Where multiple grips are used such as in FIG. 4, the lengths of each grip body 18 are approximately half the length of the stent 20 or less. In at least one embodiment the diameter of the grips taper from a larger diameter at the ends 34 of the stent 20 to a smaller diameter under the body 36 of the stent 20.

In some embodiments of the invention stent 20 is a self-expandable device such as are known. Stent 20 may be at least partially constructed from nickel, titanium, stainless steel, other metals and alloys thereof, such as nitinol. Other materials suitable for use in constructing stent 20 may include shape memory polymers, etc.

Figure 6:
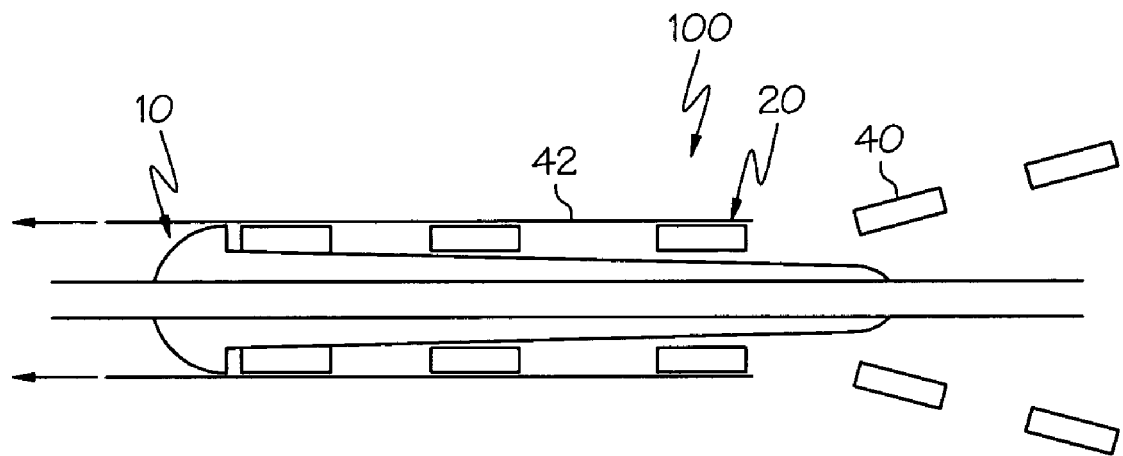
FIGS. 6 and 7 are close up cross-sectional side views of an embodiment of the invention shown during a stent delivery process.
Figure 7:
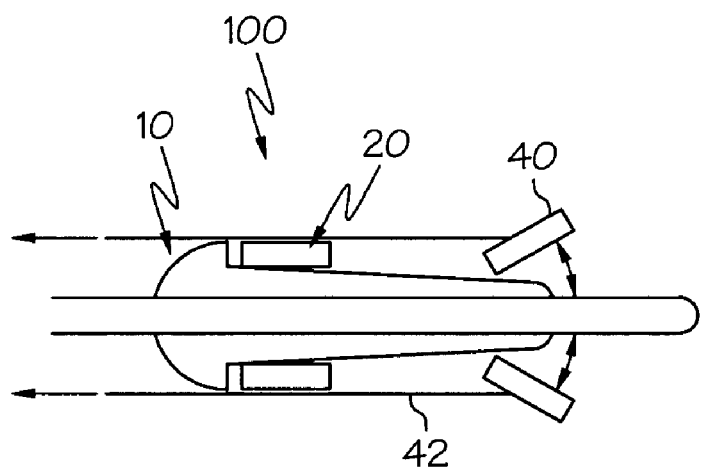

In the various embodiments of the invention, the grip 10 effectively reduces the longitudinal aspect of the catheter to stent force by ensuring that the individual struts 40 of the stent 20 are at a shallower or smaller angle upon exiting the confines of a sheath, sleeve or other stent retaining device 42 when the sheath 42 is retracted to allow the stent 20 to expand such as is shown in FIGS. 6 and 7.

In some embodiments, a grip 10 is at least partially constructed of a polymer material. In some embodiments the material has a Shore-A durometer value of about 60 to about 90 and in some embodiments about 70 to about 90. In some embodiments the grip is at least partially constructed from one or more materials such as: polyether ester; HYTREL (polyether-ester copolymer) by Du Pont Co.; polyether block amides; ARNITEL (polyether-ester copolymer) by DSM Engineering Plastics; PELLETHANE (polyurethane with polyester, polyether, or polycaprolactone copolymers) by Dow Chemical; polyurethane; aromatic polyether based polyurethanes, such as TECOTHANE available from Thermedics Inc.; silicon, rubber, or foam, etc.

In at least one embodiment the grip 10 is at least partially constructed from a radiopaque polymer or other radiopaque material.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent delivery system comprising:
   a catheter, the catheter having an inner shaft and a retractable sheath, the inner shaft having at least one grip member engaged to a portion of the inner shaft nearer a distal end of the inner shaft than a proximal end of the inner shaft, the at least one grip member comprising a body region and a hub region, the body region being tapered from a first end to a second end, the hub region being adjacent to the first end of the body region, an outer diameter of the hub region being greater than an outer diameter of the first end of the body region; and
   a stent, the stent being expandable from an unexpanded state to an expanded state, in the unexpanded state, at least a portion of the stent being disposed about a portion of the inner shaft and engaged to at least a portion of the body region of the at least one grip and the hub region of the at least one grip member being positioned between the stent and the proximal end of the inner shaft, in the unexpanded state, the retractable sheath overlying the stent, wherein the stent expands to the expanded state when the retractable sheath is retracted off of the stent,
   wherein the grip member is configured so that the stent directly contacts the hub region when the sheath is retracted.

2. The stent delivery system of claim 1 wherein the stent comprises a plurality of struts.

3. The stent delivery system of claim 2 wherein the catheter exerts a longitudinal force upon individual struts of the stent when the sheath is retracted from about the stent, the at least one grip member reducing the longitudinal force the catheter exerts on the individual struts.

4. The stent delivery system of claim 1 wherein the at least one grip member comprises a first grip member and a second grip member, an end of the body region of the first grip member being substantially adjacent to an end of the body region of the second grip member.

5. The stent delivery system of claim 4 wherein the stent comprises a first end portion, a second end portion and a body portion therebetween, in the unexpanded state the first end portion of the stent being engaged to at least a portion of the body region of the first grip member, and the second end portion of the stent being engaged to at least a portion of the body region of the second grip member.

6. The stent delivery system of claim 5 wherein, in the unexpanded state, the body portion of the stent overlies the end of the body region of the first grip member and the end of the body region of the second grip member.

7. The stent delivery system of claim 1 wherein the at least a portion of the body region of the at least one grip member has a hardness of about 60 to about 90 as measured on the Shore A hardness scale.

8. The stent delivery system of claim 1 wherein the at least a portion of the body region of the at least one grip member has a hardness of about 70 to about 90 as measured on the Shore A hardness scale.

9. The stent delivery system of claim 1 wherein the at least a portion of the body region of the at least one grip member is constructed from at least one material of the group consisting of: polyether ester, polyether block amides, PELLETHANE, TECOTHANE, polyurethane, rubber foam, silicon and any combination there of.

10. The stent delivery system of claim 1 wherein the at least a portion of the body region of the at least one grip member is radiopaque.

11. A method, comprising:
    providing a grip between a catheter shaft and an outer sheath, the grip being nearer a distal end of the catheter shaft than a proximal end of the catheter shaft, the grip comprising a body region and a hub region, the body region being tapered from a first end to a second end, the hub region being adjacent to the first end of the body region, an outer diameter of the hub region being greater than an outer diameter of the first end of the body region;
    providing a stent between the body region of the grip and the outer sheath, the hub region of the grip being positioned between the stent and the proximal end of the catheter shaft; and
    retracting the outer sheath relative to the catheter shaft, wherein the stent directly contacts the hub region when the outer sheath is retracted.

12. The method of claim 11 further comprising engaging at least a portion of the stent in an unexpanded state to at least a portion of the body region of the grip.

13. The stent delivery system of claim 1, wherein the at least one grip member is at least partially constructed from a polymeric material.

14. The method of claim 11, wherein the grip is at least partially constructed from a polymeric material.

15. The stent delivery system of claim 1, wherein the outer diameter of the hub region is greater than an outer diameter of the stent when the stent is in its unexpanded state.

16. The method of claim 11, wherein the outer diameter of the hub region is greater than an outer diameter of the stent when the stent is in an unexpanded state.

* * * * *